(12) United States Patent
Soriano et al.

(10) Patent No.: US 8,600,487 B2
(45) Date of Patent: Dec. 3, 2013

(54) SYSTEM AND METHOD FOR EXPLOITING ATRIAL ELECTROCARDIAC PARAMETERS IN ASSESSING LEFT ATRIAL PRESSURE USING AN IMPLANTABLE MEDICAL DEVICE

(75) Inventors: Alex Soriano, Ventura, CA (US); Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 953 days.

(21) Appl. No.: 12/713,019

(22) Filed: Feb. 25, 2010

(65) Prior Publication Data
US 2011/0208077 A1      Aug. 25, 2011

(51) Int. Cl.
*A61B 5/0452*      (2006.01)
(52) U.S. Cl.
USPC .............................. 600/513; 607/18; 607/23
(58) Field of Classification Search
USPC .......................................... 600/509, 516, 513
See application file for complete search history.

(56) References Cited

U.S. PATENT DOCUMENTS

| | | | |
|---|---|---|---|
| 5,800,467 A | 9/1998 | Park et al. | |
| 5,991,661 A | 11/1999 | Park et al. | |
| 6,480,733 B1 | 11/2002 | Turcott | |
| 6,512,952 B2 | 1/2003 | Stahmann et al. | |
| 6,572,557 B2 | 6/2003 | Tchou et al. | |
| 6,622,045 B2 | 9/2003 | Snell et al. | |
| 6,628,988 B2 | 9/2003 | Kramer et al. | |
| 6,643,546 B2 | 11/2003 | Mathis et al. | |
| 6,643,548 B1 | 11/2003 | Mai et al. | |
| 6,741,885 B1 | 5/2004 | Park et al. | |
| 6,748,261 B1 | 6/2004 | Kroll et al. | |
| 7,115,096 B2 | 10/2006 | Siejko et al. | |
| 2003/0069609 A1* | 4/2003 | Thompson | 607/14 |
| 2005/0080460 A1* | 4/2005 | Wang et al. | 607/17 |
| 2008/0262361 A1 | 10/2008 | Gutfinger et al. | |
| 2009/0018597 A1 | 1/2009 | Wenzel et al. | |
| 2009/0299423 A1* | 12/2009 | Min | 607/9 |

FOREIGN PATENT DOCUMENTS

EP      1977785 B1      1/2010

OTHER PUBLICATIONS

Song, Jessica Pharm D. et al., "Effect of Diuresis on P-Wave Duration and Dispersion," Pharmacotherapy. 2002:22(5):564-568.

* cited by examiner

*Primary Examiner* — Carl H Layno
*Assistant Examiner* — Paula J Stice

(57) ABSTRACT

Techniques are provided for assessing left atrial pressure (LAP) based on atrial electrocardiac signal parameters, particularly intra-atrial conduction delay (IACD) and P-wave duration. In one example, a pacemaker or other implantable device senses an intracardiac electrogram (IEGM) or a subcutaneous electrocardiogram (ECG), from which IACD and P-wave duration are derived. The device tracks changes, if any, in the parameters. A significant increase in either IACD or P-wave duration is associated with an increase in LAP. In some examples, conversion factors are calibrated for use with a particular patient to relate IACD and/or P-wave duration values to LAP values to provide an estimate of actual LAP. The conversion factors are pre-calibrated using LAP measurements obtained using a wedge pressure sensor. In other examples, IACD and P-wave duration are instead used to confirm the detection of an elevation in LAP initially made using impedance signals. Other confirmation parameters are described as well.

11 Claims, 9 Drawing Sheets

SYSTEM AND METHOD FOR EXPLOITING ATRIAL ELECTROCARDIAC PARAMETERS IN ASSESSING LEFT ATRIAL PRESSURE USING AN IMPLANTABLE MEDICAL DEVICE

FIELD OF THE INVENTION

The invention generally relates to implantable medical devices, such as pacemakers, implantable cardioverter defibrillators (ICDs) and subcutaneous (sub-Q) monitors, and in particular to techniques for detecting changes in left atrial pressure (LAP) using such devices.

BACKGROUND OF THE INVENTION

Heart failure is a debilitating disease in which abnormal function of the heart leads to inadequate blood flow to fulfill the needs of the tissues and organs of the body. Typically, the heart loses propulsive power because the cardiac muscle loses capacity to stretch and contract. Often, the ventricles do not adequately fill with blood between heartbeats and the valves regulating blood flow become leaky, allowing regurgitation or back-flow of blood. The impairment of arterial circulation may deprive vital organs of oxygen and nutrients. Fatigue, weakness and the inability to carry out daily tasks may result. Not all heart failure patients suffer debilitating symptoms immediately. Some may live actively for years. Yet, with few exceptions, the disease is relentlessly progressive.

As heart failure progresses, it tends to become increasingly difficult to manage. Even the compensatory responses it triggers in the body may themselves eventually complicate the clinical prognosis. For example, when the heart attempts to compensate for reduced cardiac output, it adds cardiac muscle mass causing the ventricles to grow in volume in an attempt to pump more blood with each heartbeat, i.e. to increase the stroke volume. This places a still higher demand on the heart's oxygen supply. If the oxygen supply falls short of the growing demand, as it often does, further injury to the heart may result, typically in the form of myocardial ischemia or myocardial infarction. The additional muscle mass may also stiffen the heart walls to hamper rather than assist in providing cardiac output. Often, electrical and mechanical dyssynchronies develop within the heart such that the various chambers of the heart no longer beat in a synchronized manner, degrading overall cardiac function. A particularly severe form of heart failure is congestive heart failure (CHF) wherein the weak pumping of the heart or compromised filling leads to build-up of fluids in the lungs and other organs and tissues.

Pulmonary edema (PE) is a swelling and/or fluid accumulation in the lungs often caused by heart failure. Briefly, the poor cardiac function resulting from heart failure can cause blood to back up in the lungs, thereby increasing blood pressure in the lungs, particularly pulmonary venous pressure. The increased pressure pushes fluid—but not blood cells—out of the blood vessels and into lung tissue and air sacs (i.e. the alveoli). This can cause severe respiratory problems and, left untreated, can be fatal. PE can also arise due to other factors besides heart failure, such as infections.

In view of the potential severity of CHF/PE, it is highly desirable to detect the conditions so that appropriate therapy can be provided. Many patients susceptible to CHF and PE are candidates for pacemakers, ICDs, cardiac resynchronization therapy (CRT) devices or sub-Q monitors such as implantable loop recorders (ILRs). Accordingly, it would be helpful to provide techniques for detecting and tracking CHF and/or PE using such implantable devices.

One useful parameter for detecting and tracking CHF/PE is LAP, i.e. the blood pressure within the left atrium of the patient. Reliable detection or estimation of LAP would permit the implanted device to track fluid overloads associated with CHF/PE for diagnostic purposes and to also control therapies such as the administration of diuretics in response to PE or the delivery of CRT in response to heart failure.

However, LAP is a difficult parameter to detect since it is not clinically appealing to place a blood pressure sensor directly in the left atrium due to the chronic risk of thromboembolic events, as well as risks associated with the transseptal implant procedure itself. Accordingly, various techniques have been developed for estimating LAP based on other parameters that can be more safely sensed by an implantable medical device. In particular, a number of techniques have been developed that use electrical impedance (Z) to estimate LAP. For example, intracardiac impedance can be sensed along a sensing vector passing through the left atrium, such as between an electrode mounted on a left ventricular (LV) lead and another electrode mounted on a right atrial (RA) lead. The impedance is affected by the blood volume inside the left atrium, which is in turn reflected by the pressure in the left atrium. Accordingly, there is a correlation between the detected impedance and LAP, which can be exploited to estimate LAP and also track CHF and fluid overloads associated with PE.

Techniques for exploiting impedance measurements to estimate LAP are referred to herein as zLAP estimation techniques. See, for example, U.S. Provisional Patent Application No. 60/787,884 of Wong et al., entitled, "Tissue Characterization Using Intracardiac Impedances with an Implantable Lead System," filed Mar. 31, 2006, and U.S. patent application Ser. Nos. 11/558,101; 11/557,851; 11/557,870; 11/557,882; and 11/558,088, each entitled "Systems and Methods to Monitor and Treat Heart Failure Conditions," of Panescu et al. See, also, U.S. patent application Ser. No. 11/558,194, by Panescu et al., entitled "Closed-Loop Adaptive Adjustment of Pacing Therapy based on Cardiogenic Impedance Signals Detected by an Implantable Medical Device."

Particularly effective techniques for calibrating zLAP estimation techniques are set forth in: U.S. patent application Ser. No. 11/559,235, by Panescu et al., entitled "System and Method for Estimating Cardiac Pressure Using Parameters Derived from Impedance Signals Detected by an Implantable Medical Device" and U.S. patent application Ser. No. 12/109,304, filed Apr. 25, 2008, of Gutfinger et al., entitled "System and Method for Calibrating Cardiac Pressure Measurements derived from Signals Detected by an Implantable Medical Device."

Although early zLAP preclinical data has demonstrated promising results, impedance-based estimates of LAP are still susceptible to non-cardiogenic influences on impedance, such as pneumonia. Accordingly, it would be desirable to develop LAP detection techniques that do not rely exclusively on impedance but additionally or alternatively exploit other parameters detectable by implantable devices to assess LAP. It is to this end that various aspects of the present invention are directed.

Rather than estimating LAP based on zLAP, techniques have been developed that estimate LAP based on conduction delays measured within electrocardiac signals. See, U.S. patent application Ser. Nos. 11/779,350 and 11/779,380, of Wenzel et al., filed Jul. 18, 2007, and both entitled "System and Method for Estimating Cardiac Pressure based on Cardiac Electrical Conduction delays using an Implantable Medical Device." Techniques are described therein for estimating LAP or other cardiac performance parameters based on measured interventricular (RV-LV) conduction delays or atrioventricular (AV) conduction delays. Predetermined conversion factors stored within the device are used to convert measured conduction delays into LAP values.

It would be desirable to develop techniques that exploit still other electrocardiac intervals or other electrocardiac morphological parameters to detect LAP, and it is to this end that various other aspects of the present invention are directed.

SUMMARY

In accordance with an exemplary embodiment, a method and system are provided for use by an implantable medical device for implant within a patient. In one example, electrocardiac signals are sensed within the patient. Atrial parameters are detected within the electrocardiac signals that are affected by LAP, such as an intra-atrial conduction delay (IACD) or an atrial depolarization event (i.e. P-wave) duration. Changes in LAP are then detected within the patient based on the atrial parameters.

In an illustrative embodiment, the implantable device is a pacemaker, ICD, CRT, ILR or Sub-Q device, which is equipped to detect intracardiac electrogram (IEGM) or subcutaneous electrocardiogram (ECG) signals from which IACDs and P-wave duration are derived. An increase in IACD is associated with an increase in LAP. Likewise, an increase in P-wave duration is associated with an increase in LAP. In this regard, it has been found that both IACD and P-wave duration increase with increasing LAP, probably due to mechanical stress. As such, these parameters are useful in detecting increases in LAP. In some examples, conversion factors are calibrated for use with a particular patient to relate IACD and/or P-wave duration values to LAP values so as to provide an actual estimate of LAP. Such conversion factors can be calibrated in advance using LAP measurements obtained, for example, using a wedge pressure sensor.

In another illustrative embodiment, the atrial parameters are instead used to confirm the detection of a change in LAP obtained based on impedance measurements. In one example, impedance (Z) signals are sensed within the patient and LAP is estimated based on impedance (zLAP). Atrial parameters affected by LAP are detected within IEGM or subcutaneous ECG signals, such as IACD and P-wave duration. Any significant changes in LAP initially detected based on impedance measurements (i.e. based on zLAP) are then confirmed using the atrial parameters.

In one particular example, the device initially detects a significant elevation in LAP (indicative of a possible fluid overload due to heart failure) by comparing zLAP to a suitable pressure threshold. The device confirms the elevation in LAP by examining changes, if any, in IACD and/or P-wave duration. As noted, IACD and P-wave duration both increase with increasing LAP. In one specific embodiment, the device detects numerical deviations in IACD and/or P-wave duration and compares the deviations to corresponding standard deviation-based thresholds, set to two-standard deviations. If deviations in the atrial parameters exceed the corresponding thresholds, the elevation in LAP is thereby confirmed and appropriate action is taken to address the high LAP. In contrast, if the atrial parameters do not change significantly with increasing LAP, then the increase in LAP is disconfirmed. In this regard, the elevation in LAP initially detected based on changes in impedance might instead have been due to other factors affecting impedance unrelated to changes in actual LAP, such as impedance changes due to the presence of pneumonia. That is, the LAP of the patient might not actually have increased.

Additional parameters may also be used to help confirm the detection of an elevated LAP. For example, heart sounds may be monitored for use in detecting any on-going left ventricular (LV) overload. If an on-going LV overload is detected, this helps confirm the elevation in LAP, since an increase in LAP is often associated with LV overloaded. In one particular example the device detects one or more of: an increased energy of a third heart sound (S3); a prolonged R-wave to first heart sound (S1) interval; a prolonged first heart sound (S1) to second heart sound (S2) interval; a reduction in S1 intensity; and an decrease in the amplitude of a double integral of S1; any of which is indicative of LV overload.

Yet other parameters that can be used to confirm an elevated LAP include changes in one or more of: heart contractility, systolic time intervals, and stroke volumes, assuming the device is equipped to detect such parameters. Still further, the device can use R-waves in conjunction with the slope (i.e. the time rate of change) of impedance signals to confirm LAP elevation. For example, the device detects R-waves while also tracking dZ/dt to identify minimum values of dZ/dt within each heartbeat. The device tracks changes, if any, in an interval between the R-wave and minimum (dZ/dt.) Significant changes in this interval can be used to confirm the elevated LAP. Still further, changes in R-wave duration can be used to help confirm LAP elevation. AZ or dZ/dt measured between a supraventricular (SVC) coil and a Case housing electrode (also referred to as the 'can' electrode') provide a particularly good estimator of cardiac performance because this configuration detects blood ejected into the great vessels and lungs located between the SVC coil electrode and the case.

Upon confirming the elevated LAP, appropriate warning signals may be generated for alerting the patient to consult a physician. The warning signals can include "tickle" warning signals applied to subcutaneous tissue and short range telemetry warning signals transmitted to a warning device external to the patient such as a bedside monitor. The warning signals, as well as appropriate diagnostic information (such as the estimated LAP values), are preferably forwarded to the physician by the bedside monitor. Various forms of therapy may also be automatically applied or modified by the implanted system in response to the elevation in LAP, depending upon the capabilities of the system. For example, if the device is equipped to perform CRT, then CRT pacing may be initiated or otherwise controlled based on LAP. If the device is equipped to deliver LA pacing, such pacing may be selectively controlled so as to improve hemodynamics. Still further, if the implanted system is equipped with a drug pump, appropriate medications (such as diuretics) may be administered directly to the patient, depending upon the programming of the device.

The particular functions performed in response to confirmation of an elevation in LAP will depend upon the capabilities of the device. As noted, the device can comprise a pacemaker, ICD, ILR, CRT device, Sub-Q device or other implantable medical device.

Method and apparatus implementations are described herein.

BRIEF DESCRIPTION OF THE DRAWINGS

Further features and advantages of the invention may be more readily understood by reference to the following description taken in conjunction with the accompanying drawings, in which.

DESCRIPTION OF THE PREFERRED EMBODIMENTS

The following description includes the best mode presently contemplated for practicing the invention. The description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Overview of Implantable Medical System with Pacer/ICD

Figure 1:
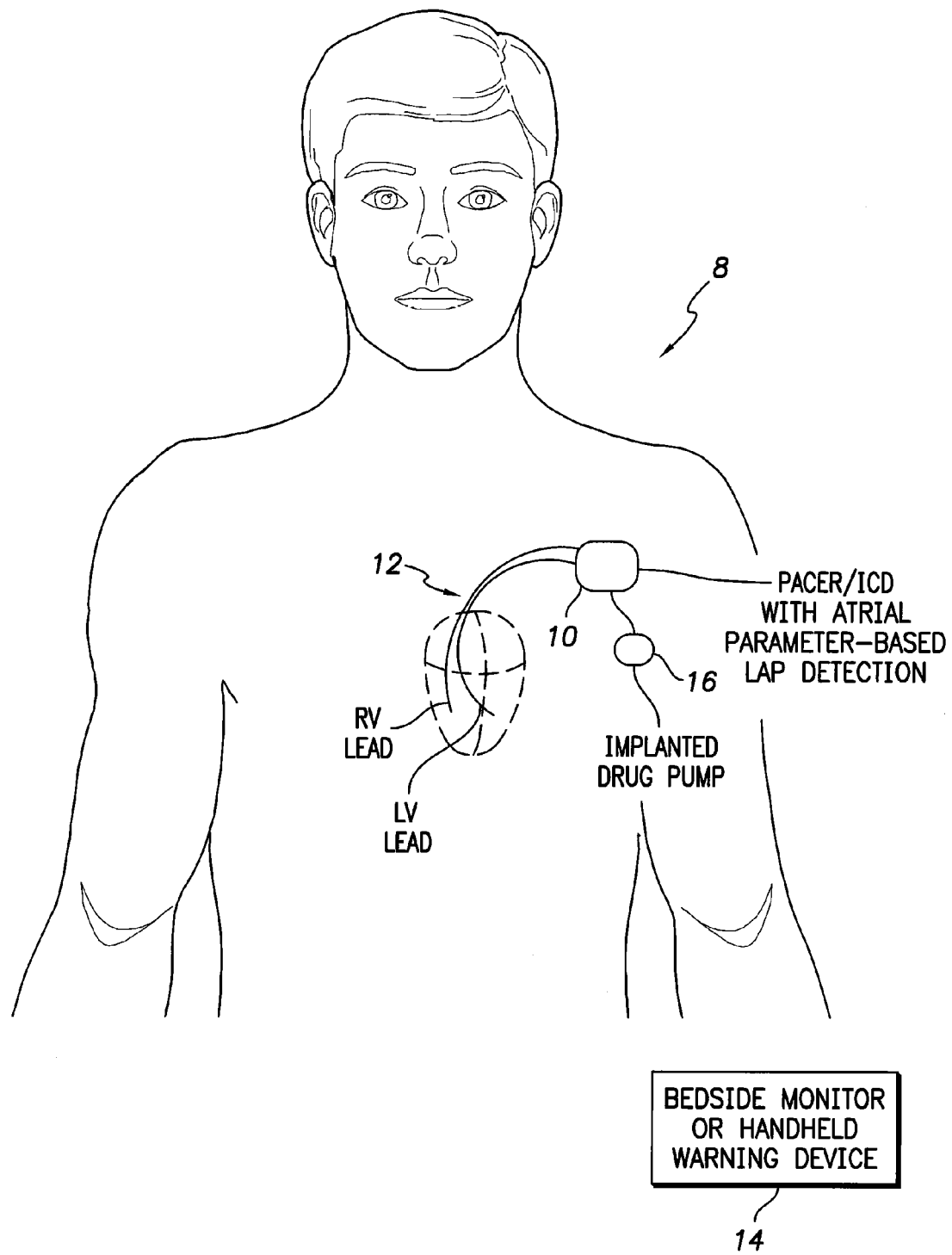
FIG. 1 is a stylized representation of an exemplary implantable medical system having a pacer/ICD equipped with atrial parameter-based LAP detection.
Figure 7:
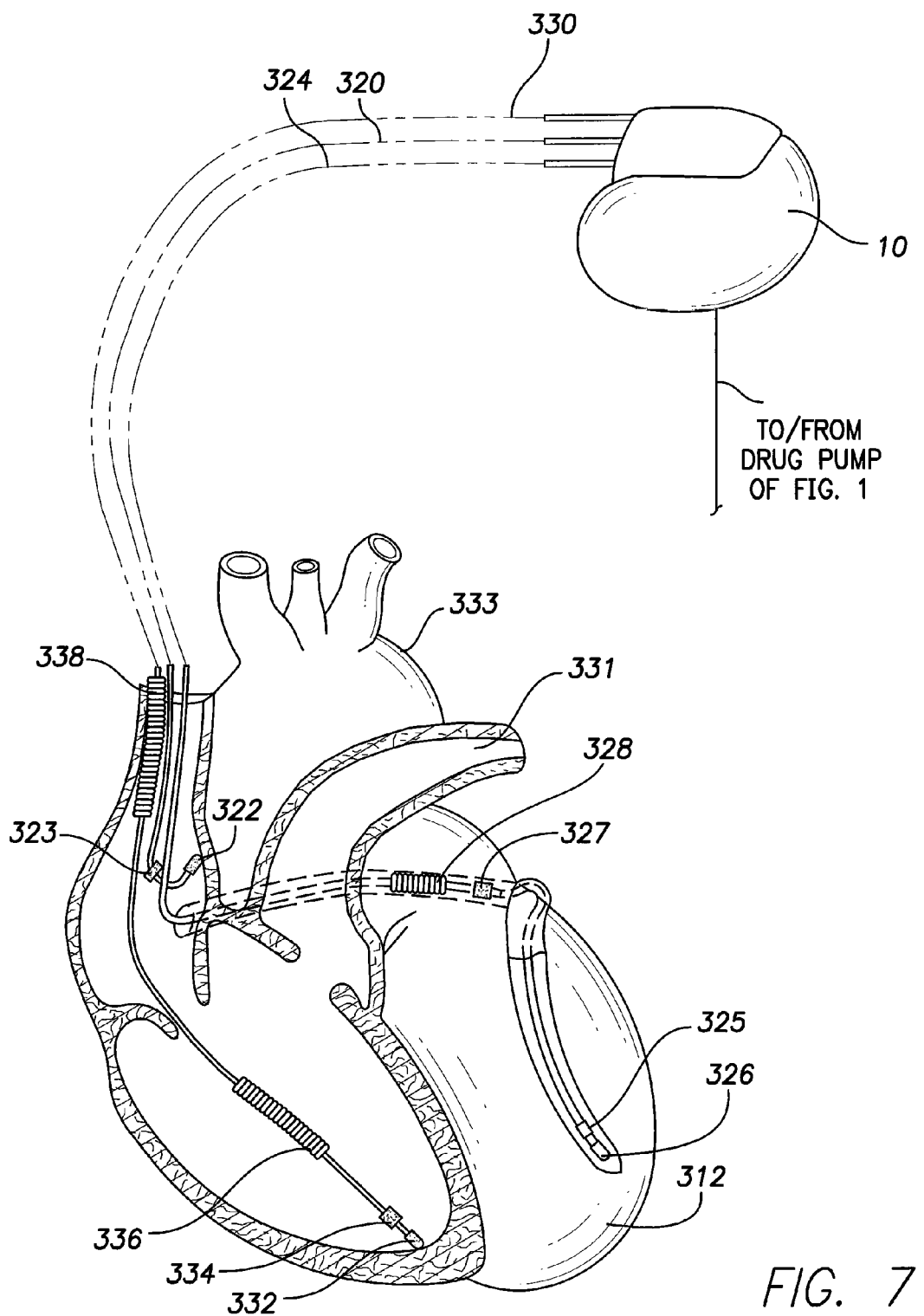
FIG. 7 is a simplified, partly cutaway view, illustrating the pacer/ICD of FIG. 1 along with a more complete set of leads implanted in the heart of the patient.

FIG. 1 provides a stylized representation of an exemplary implantable medical system 8 capable of detecting atrial electrocardiac parameters within the heart of the patient that are affected by LAP and then detecting changes in LAP based on the parameters. To this end, implantable system 8 includes a pacer/ICD 10 or other cardiac stimulation device that incorporates components for detecting IEGMs using electrodes mounted to a set of sensing/pacing leads 12. In FIG. 1, only two leads are shown. A more complete set of leads is illustrated in FIG. 7, which is discussed below. Within many of the exemplary implementations described herein, changes in LAP are detected based on changes in IACDs and/or changes in P-wave duration (or width). However, other atrial electrocardiac parameters might be exploited, alone or in combination, to detect changes in LAP so long as the parameters are affected by changing LAP. In some examples, pre-calibrated conversion factors are stored within the pacer/ICD for converting the atrial parameters into LAP values. In other examples, a significant increase or elevation in LAP is detected without necessarily estimating the actual value of LAP. In still other examples, the atrial parameters are used only to confirm the detection of a significant elevation in LAP made using other parameters, such as impedance.

Assuming a significant elevation in LAP is detected, warning signals are generated to warn the patient, using either a warning device internal to the pacer/ICD or an external bedside monitor/handheld warning device 14. The internal warning device may be a vibrating device or a "tickle" voltage device that, in either case, provides perceptible stimulation to the patient to alert the patient so that the patient may consult a physician. In one example, once the tickle warning is felt, the patient positions an external warning device above his or her chest. The handheld device receives short-range telemetry signals from the implanted device and provides audible or visual verification of the warning signal. The handheld warning device thereby provides confirmation of the warning to the patient, who may be otherwise uncertain as to the reason for the internally generated warning signal. For further information regarding such warning/notification techniques, see U.S. patent application Ser. No. 11/043,612, of Kil et al., filed Jan. 25, 2005, entitled "System and Method for Distinguishing among Ischemia, Hypoglycemia and Hyperglycemia using an Implantable Medical Device." See, also, the Merlin Mobile™ system of St. Jude Medical.

If a bedside monitor is provided, the bedside monitor provides audible or visual alarm signals to alert the patient or caregiver, as well as textual or graphic displays. In addition, diagnostic information pertaining to elevated LAP or other issues is transferred to the bedside monitor or is stored within the pacer/ICD for subsequent transmission to an external programmer (not shown in FIG. 1) for review by a physician or other medical professional. The physician may then prescribe any appropriate therapies to address the condition, such as administration of diuretics if warranted. The physician may also adjust the operation of the pacer/ICD to activate, deactivate or otherwise control any therapies that are automatically applied. The bedside monitor may be directly networked with a centralized computing system for immediately notifying the physician of any significant increase in LAP. The centralized system may include such systems as the HouseCall™ system or the Merlin@home/Merlin.Net systems of St. Jude Medical. A system incorporating bedside monitoring units connected to a centralized external programmer system is described in U.S. Pat. No. 6,622,045 to Snell et al., "System and Method for Remote Programming of Implantable Cardiac Stimulation Devices."

In addition to issuing warnings, various forms of therapy may be initiated or controlled by the pacer/ICD in response to a significant elevation in LAP. In this regard, if the implanted system is equipped with a drug pump or other medication dispensing device, appropriate medications may be automatically delivered to the patient upon detection of a significant increase in LAP. For example, diuretics may be delivered directly to the patient via the drug pump. Alternatively, if a drug pump is not available, the patient may be provided with instructions to take oral dosages of diuretics.

Still further, in some implementations, pacing therapy is initiated or adjusted in response to elevated LAP. For example, if the device is equipped to deliver pacing therapy to the LA, such pacing can be controlled in an effort to improve hemodynamics and reduce LAP.

Hence, FIG. 1 provides an overview of an implantable medical system capable of detecting elevated LAP based on atrial electrocardiac parameters and then adjusting pacing, delivering appropriate warning/notification signals, and/or selectively delivering medications, when warranted. Embodiments may be implemented that do not necessarily perform all of these functions. For example, embodiments may be implemented that detect an elevated LAP but do not automatically initiate or adjust therapy. Moreover, systems provided in accordance with the invention need not include all of the components shown in FIG. 1. In many cases, for example, the system will include only a pacer/ICD and its leads. Implantable drug pumps are not necessarily implanted. Some implementations may employ an external monitor for displaying warning signals without any internal warning device. These are just a few exemplary embodiments. No attempt is made herein to describe all possible combinations of components that may be provided in accordance with the general principles of the invention. In addition, note that the particular locations and sizes of the implanted components shown in FIG. 1 are merely illustrative and may not necessarily correspond to actual implant locations. Although internal signal transmission lines provided are illustrated in FIG. 1 for interconnecting the implanted components, wireless signal transmission may alternatively be employed.

Techniques for Detecting Changes in LAP Using Atrial Electrocardiac Parameters

Figure 2:
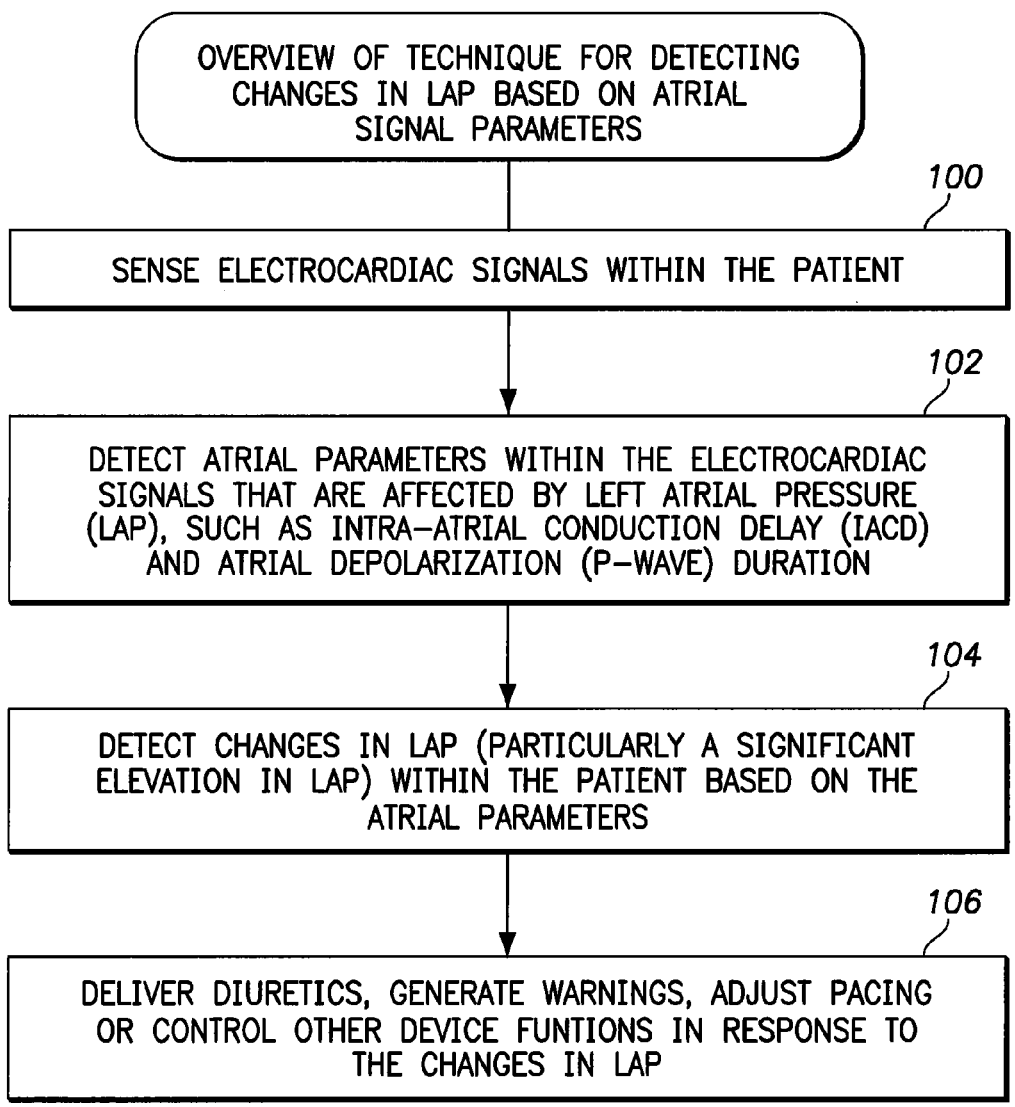
FIG. 2 is a flow diagram providing a broad overview of a technique for detecting changes in LAP based on atrial electrocardiac parameters, which can be performed by the system of FIG. 1.

FIG. 2 provides an overview of techniques that can be performed by the pacer/ICD of FIG. 1 or other implantable medical device for detecting a significant change in LAP. At step 100, the pacer/ICD senses electrocardiac signals within the patient using suitable leads and, at step 102, detects atrial parameters within the signals that are affected by LAP, such as IACD and P-wave duration. The P-wave represents an atrial depolarization event. (Note that, in some of the medical literature, the term P-wave is only used to refer to atrial depolarization as manifest with a surface ECG. Herein, the term P-wave additionally applies to the atrial depolarization waveform as detected within an IEGM or within a subcutaneous ECG.) Techniques for detecting IACD and P-wave duration will be described in further detail below. Herein, the term P-wave includes P-waves that are spontaneous or triggered by pacing the atria. Atria refers to either the right or left atrium and pacing pulses may be delivered to either atria from specific locations. For consistency, it may be preferable to use a pacing pulse to trigger the P-wave in order to establish a specific interval between P-waves and establishing a specific site for pacing so that the P-wave attributes will be consistent as possible each time the P-wave is measured. Additionally, the state of the patient (exercising, resting, sleeping, etc.) may be detected using a sensor (such as an activity sensor) and used to determine when the P-wave measurement is made. For example, taking a measurement while the patient is resting will improve reproducibility of the P-wave features. Making the measurement when a patient is in a particular posture will also improve consistency and help discern relative changes in the P-wave features. The posture of the patient (supine, prone, sitting, upright, etc.) can be determined using a 3D accelerometer. Finally, precision and consistency may be improved by considering the time or the frequency of the P-wave measurement. Measuring the P-wave features once and hour over each day will substantially cancel out diurnal variation by using averaging over, e.g., twenty-four measurements made throughout the day or measurements may be made at a specific or at specific times of the day. For instance, measurements made at 3:00 a.m. will typically provide a high degree of consistency because the patient is likely to be quiet and the posture will likely be supine and the LAP will likely be most elevated because this position elevates cardiac preload.

At step 104, the pacer/ICD detects changes in LAP (particularly a significant elevation in LAP) within the patient based on the atrial parameters obtained at step 102, such as by comparison of the IACD and P-wave duration values against suitable thresholds. Examples where the thresholds are based on standard deviations are described below. Alternatively, other thresholds can instead be exploited, such as percentage-based thresholds. Yet another alternative is to establish a threshold is to provide a training period over a few days to a month in which the range of the excursions in the P-wave features are recorded during this time. It is important that the patient be under careful medical supervision with respect to diet and overall medical care As noted, the IACD and P-wave duration tend to increase with increasing LAP, probably due to mechanical stress. See, for example, Song et al., "Effect of Diuresis on P-Wave Duration and Dispersion," Pharmacotherapy 22(5):564-568, 2002. In this study, twenty-one patients with decompensated heart failure were assessed post emergency room (ER) admission using twelve-lead ECGs to obtain baseline P-wave durations. Following diuresis of 3±1 L of fluid after 40+/−23 hours, a twelve lead ECG was repeated to assess P-wave duration. "A significant correlation was found between average P-wave duration and amount of fluid removed (r=−0.59, p=0.015)." P-wave dispersion was not affected. It is important to note that electrolytes were essentially unchanged pre- and post-diuresis. The authors showed that the P-wave duration decreased from an average of 97.3±18.1 ms at baseline to a final level of 90.5±16.1 ms. They went on to conclude, "Diuresis may attenuate electrophysiologic changes caused by fluid overload." The present inventors believe that IACD, like P-wave duration, also increases with increasing LAP.

At step 106, the pacer/ICD then delivers diuretics, generates warnings, adjusts pacing or controls other device functions in response to the changes in LAP detected at step 104. For example, diuretics such as furosemide or bumetanide can be administered to the patient in response to elevated LAP. (Diuretics are drugs that increase the flow of urine, thus eliminating water from the body, ultimately reducing fluid levels that are often elevated along with LAP.) In one example, action is taken if LAP is found to exceed 25 mmHg.

Before taking any action, the pacer/ICD can be confirm the elevated LAP using other detection techniques, such as detection techniques based on impedance measurements or based on AV or RV-LV delays. See the various patent applications cited above in the Background Section.

Figure 3:
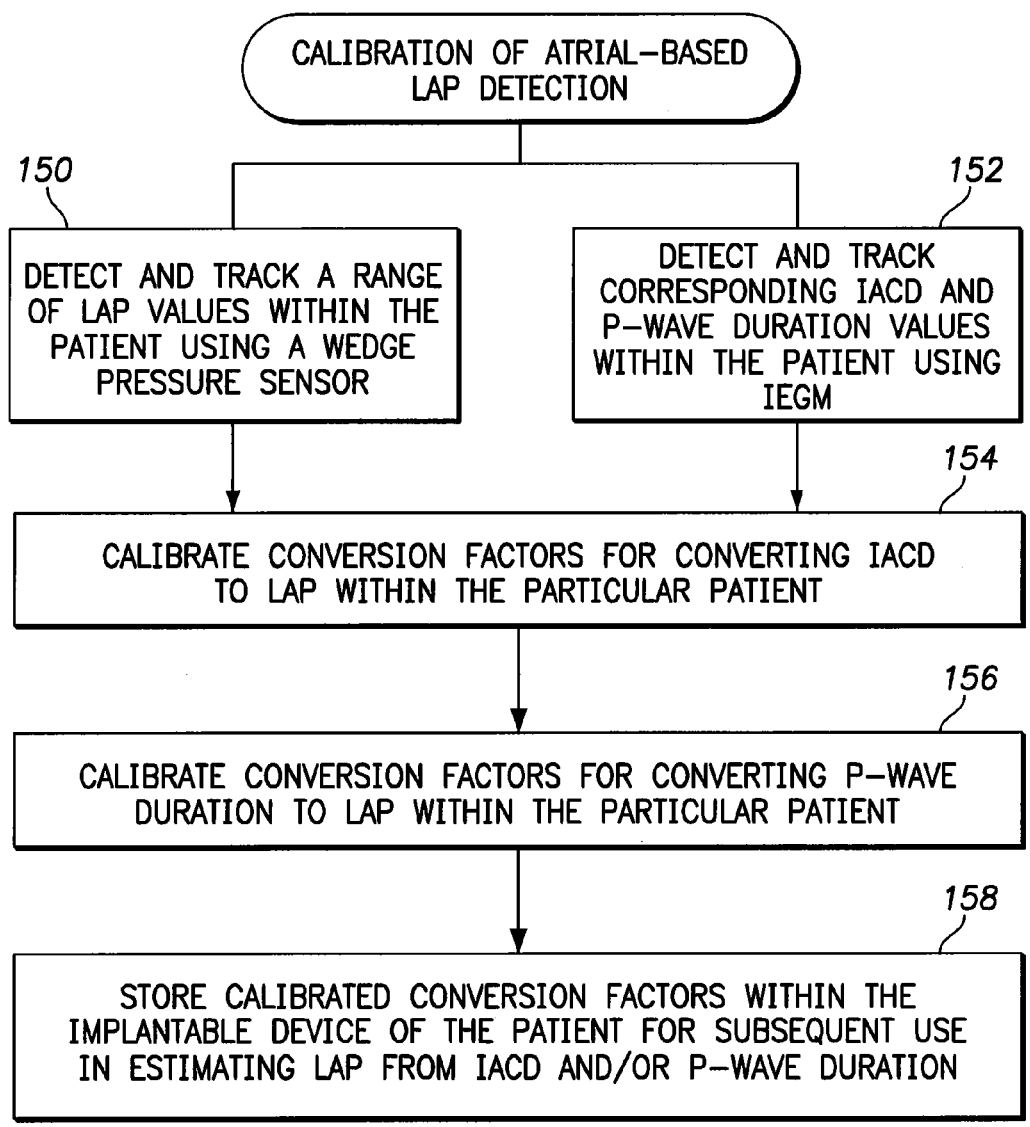
FIG. 3 summarizes a calibration method for use in calibrating the technique of FIG. 1 to provide estimates of LAP in mmHG.

FIG. 3 summarizes a technique for calibrating the atrial parameter-based LAP detection technique so that LAP can be estimated within a given patient based on IACD and/or P-wave duration detected within that patient. At step 150, LAP is detected and tracked within a given patient over a range of values using a wedge pressure sensor using, e.g., a Swan-Ganz catheter equipped to measure pulmonary capillary wedge pressure in mmHg or other appropriate units. Concurrently, at step 152, the pacer/ICD within the patient detects and tracks IACD and P-wave duration based on IEGM signals sensed therein. These steps are performed while the LAP of the patient changes over a range of values, as may be induced, for example, via the Valsalva maneuver or the like. The use of Valsalva maneuver in the calibration of LAP measurements is discussed, e.g., in U.S. patent application Ser. Nos. 11/779,350 and 11/779,380, of Wenzel et al., cited above.

At step 154, conversion factors are calibrated for converting IACD to LAP within the particular patient. That is, the conversion factors relate a given IACD value to a corresponding estimated LAP value in units of mmHg. At step 156, conversion factors are calibrated for converting P-wave duration to LAP (again in units of mmHg) within the particular patient. Again, see the Wenzel et al. applications (pertinent portions of which are incorporated herein) for suitable techniques for deriving and then exploiting calibration factors for use in estimating LAP. (In the examples of Wenzel et al., the calibration factors are primarily used for estimating LAP based on AV and LV-RV delays.) Steps 154 and 156 may be performed, for example, by an external device programmer based on data received from the pacer/ICD of the patient and from the wedge pressure sensor.

At step 158, the conversion factors are stored within the implantable medical device of the patient for subsequent use in estimating LAP based on IACD and/or P-wave duration values. Look-up tables may instead be used to provide LAP values corresponding to ranges of IACD and/or P-wave duration values. The calibration procedure of FIG. 3 can be repeated as needed to re-calibrate the conversion factors.

Techniques for Confirming Changes in zLAP Using Atrial Parameters

Figure 4:
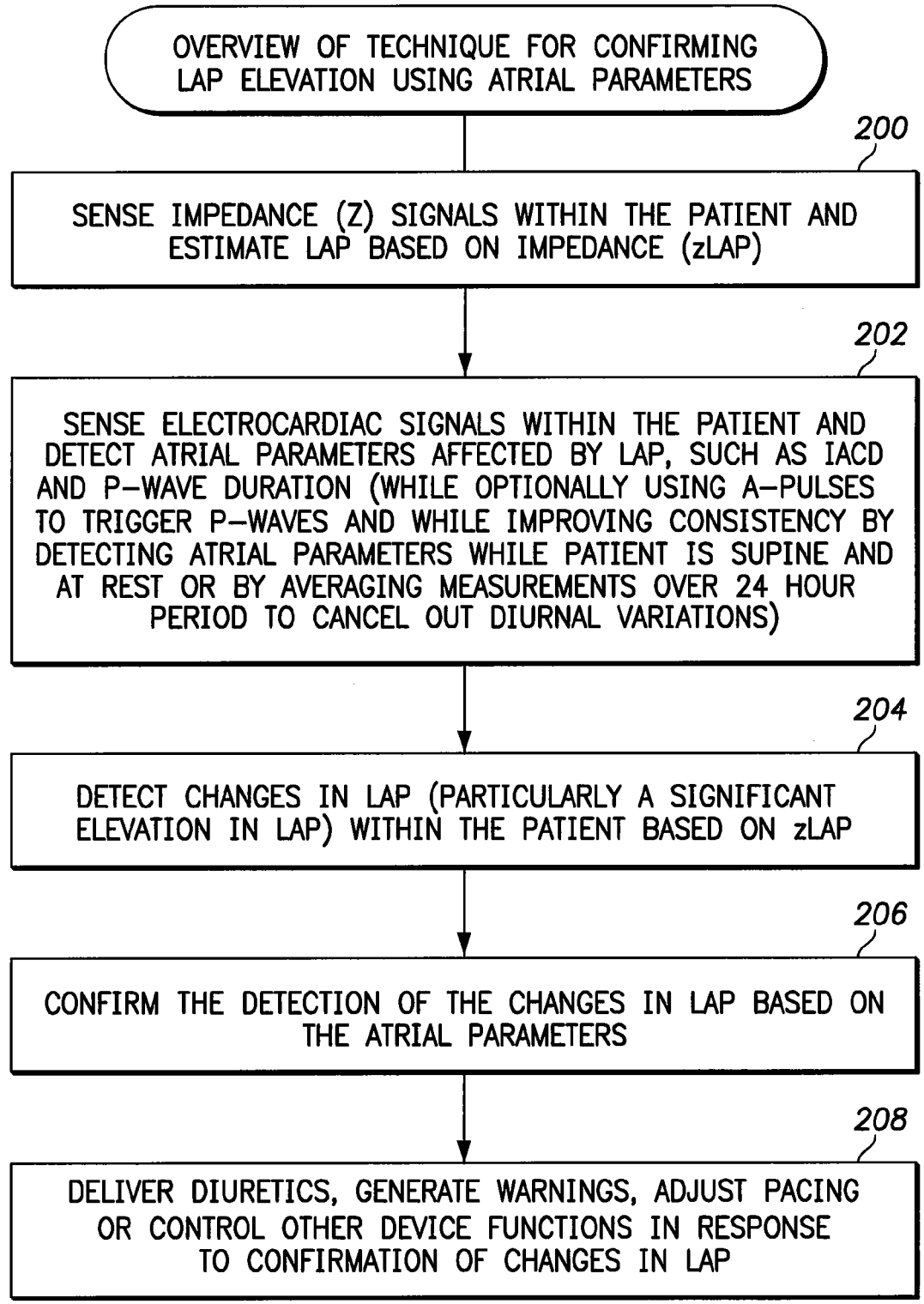
FIG. 4 is a flow diagram providing a broad overview of a technique for confirming the detection of an elevated LAP initially made based on impedance signals, wherein confirmation is achieved using atrial electrocardiac parameters, and which can also be performed by the system of FIG. 1.

FIG. 4 provides an overview of techniques that may be performed by the pacer/ICD of FIG. 1 or other implantable medical device for confirming a significant change in LAP detected using impedance. At step 200, the pacer/ICD senses impedance (Z) signals within the patient and estimates LAP based on impedance (zLAP). See, the zLAP estimation techniques cited above. At step 202, the pacer/ICD senses electrocardiac signals within the patient and detects atrial parameters affected by LAP, such as IACD and P-wave duration. (while optionally using A-pulses to trigger P-waves and while improving consistency by detecting atrial parameters while patient is supine and at rest or by averaging measurements over twenty-four hour period to cancel out diurnal variations, as discussed above).

At step 204, the pacer/ICD detects changes in LAP (particularly a significant elevation in LAP) within the patient based on zLAP and then, at step 206, confirms the detection of the changes in LAP based on the atrial parameters. Exemplary confirmation techniques exploiting standard deviation-based thresholds are described below with reference to the example of FIG. 5. At step 208, the pacer/ICD then delivers diuretics, generates warnings, adjusts pacing or controls other device functions in response to confirmation of changes in LAP.

By using IACD and/or P-wave duration to confirm a zLAP-based detection of elevated LAP, circumstances can be avoided wherein an increase in zLAP due to non-cardiogenic factors might trigger unnecessary device responses. For example, if impedance increases due to pulmonary congestion from pneumonia, such might result in an increase in zLAP. Without the independent confirmation provided by the technique of FIG. 4, the device might respond by delivering inappropriate therapy under the circumstances, such as by delivering certain forms of pacing therapy appropriate only for a cardiogenic increase in LAP. Additional confirmation parameters are described below with reference to FIG. 6, which can be used to provide additional confirmation before therapeutic action is taken.

Figure 5:
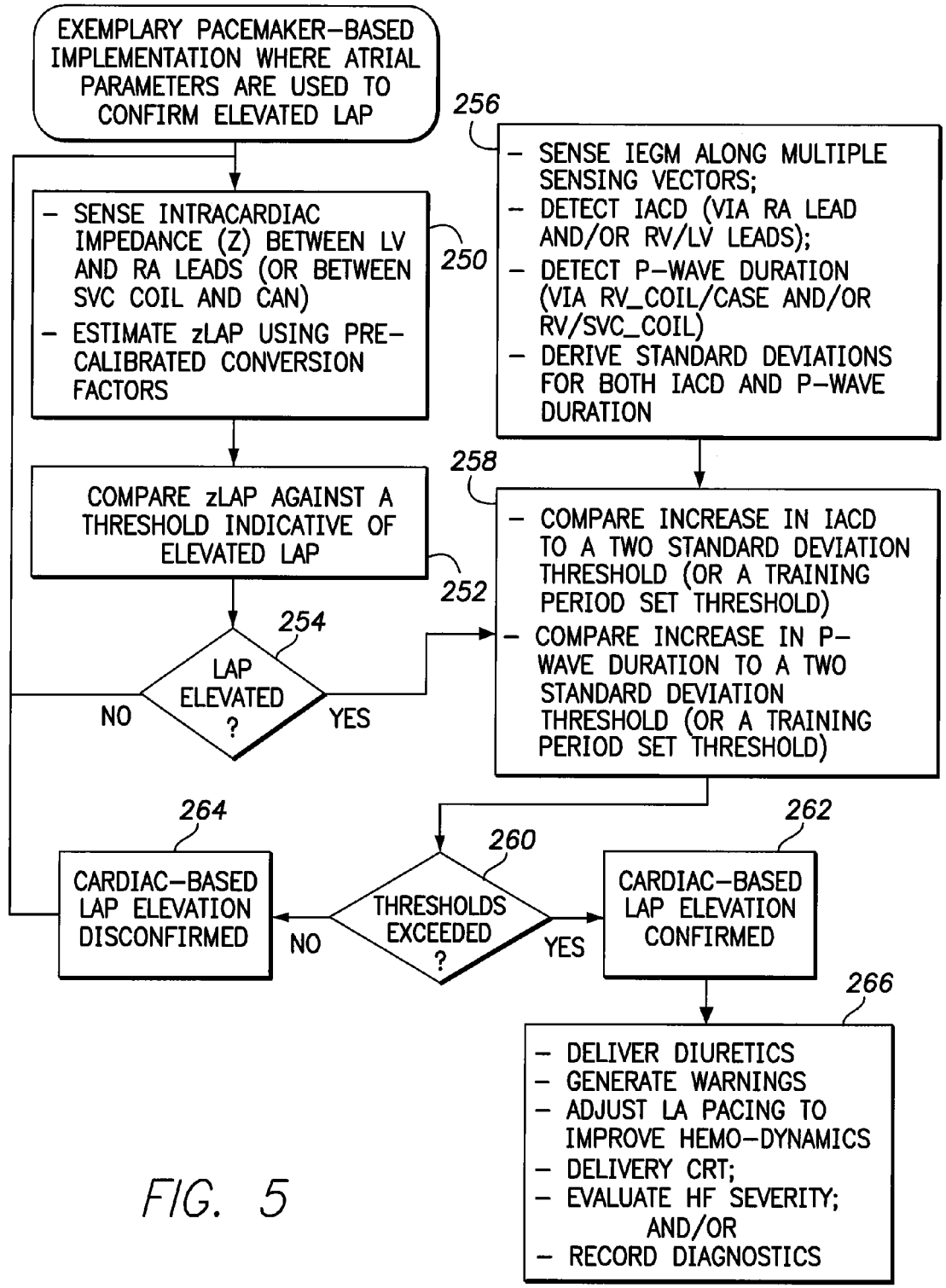
FIG. 5 is a flow diagram summarizing an illustrative technique performed in accordance with the confirmation technique of FIG. 4 wherein deviations in IACD and/or P-wave duration are used to confirm an elevated LAP.

Turning now to FIG. 5, an exemplary confirmation technique will be described in greater detail. Beginning at step 250, senses intracardiac impedance (Z) between LV and RA leads and then estimates zLAP using pre-calibrated conversion factors (or between the SVC coil and device housing, as noted above.) A particularly effective tri-phasic impedance detection pulse for use in detecting impedance is described in U.S. patent application Ser. No. 11/558,194, cited above. However, other impedance detection pulses or waveforms may instead be exploited. At step 252, the pacer/ICD compares zLAP against a threshold indicative of elevated LAP. In one example, the threshold is set to 25 mmHg. So long as zLAP does not exceed the threshold, the pacer/ICD simply repeats steps 250-252 to continue to monitor for changes in zLAP (while, of course, performing any other needed pacing/sensing/shocking functions not shown in the figure).

If zLAP exceeds the threshold, then the pacer/ICD seeks to confirm the elevated LAP by using IACD and P-wave duration. That is, at step 256, the pacer/ICD: senses IEGMs along multiple sensing vectors; detects IACD (via the RA lead and/or RV/LV leads); detects P-wave duration (via RV_COIL/CASE and/or RV/SVC_COIL); and derives standard deviations for both IACD and P-wave duration from patient baselines. The particular IEGM signals to be used to detect IACD and P-wave duration may depend upon the particular leads implanted within the patient and sensing capabilities of the device. For example, P-waves can be captured from far-field shocking coils, RV ring, and RV tip electrodes measured to the case. In addition, not only P-waves but also IACD may be measured using systems incorporating right-sided and left-sided leads. For instance, the RA depolarization can be measured with an RA lead while LA depolarization can be assessed LV to Case. This provides a very effective means of precisely measuring and monitoring the IACD.

Figure 9:
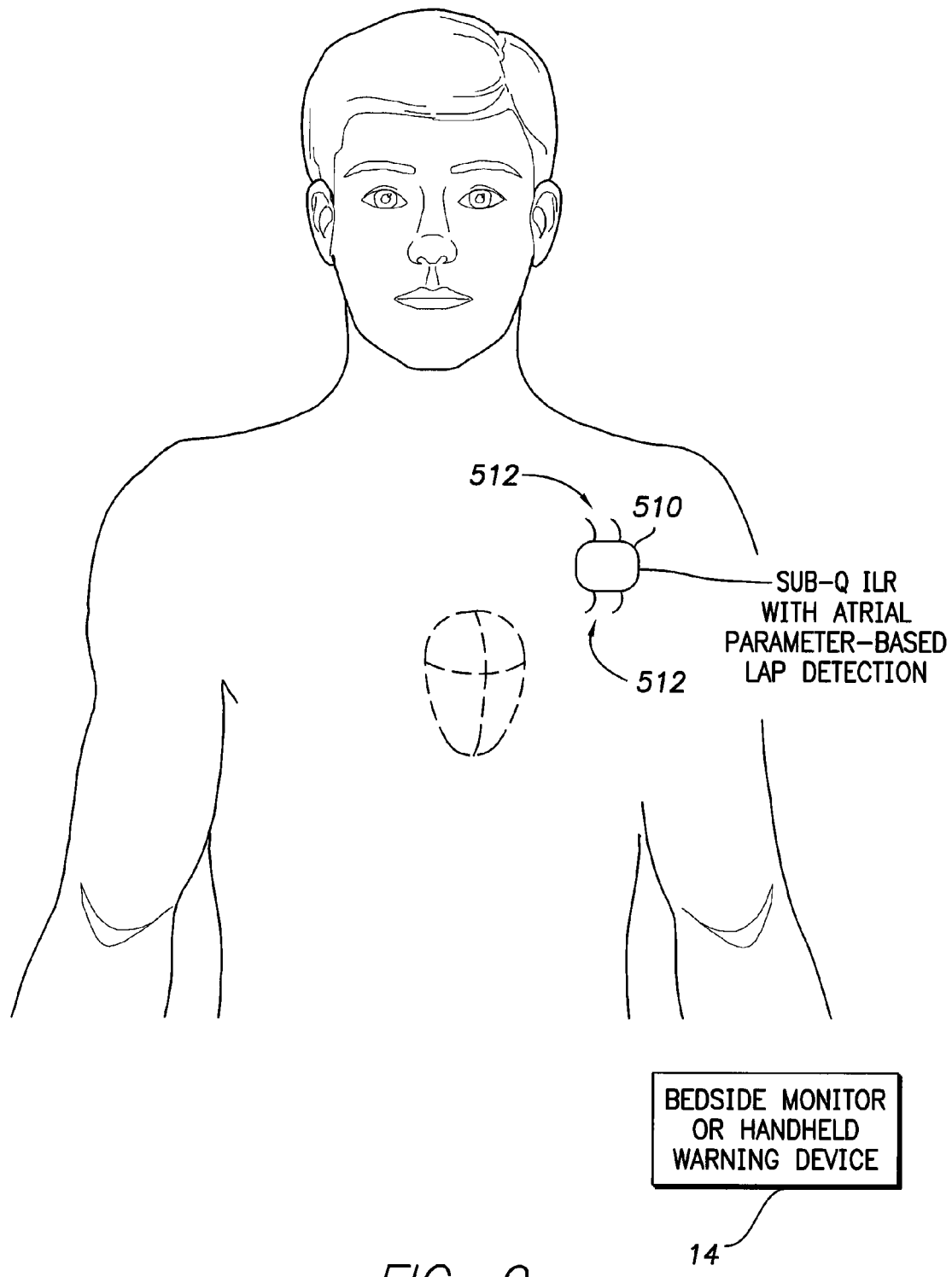
FIG. 9 is a stylized representation of an exemplary implantable medical system having a Sub-Q ILR equipped with atrial parameter-based LAP detection.

The P-wave morphology captured using signal averaging techniques using the R-wave as a retrospective trigger point is a valuable tool in assessing P-wave duration. The duration of signal-averaged P-waves can also be precisely estimated from electrograms captured using a sub-Q monitor (as shown in FIG. 9.) See, also, the various P-wave detection techniques described in U.S. patent application Ser. No. 12/267,483, by Gil et al., filed Nov. 7, 2008, entitled "System and Method for Setting Atrioventricular Pacing Delays based on Far-Field Atrial Signals" and U.S. patent application Ser. No. 12/116,450, filed May 7, 2008, of Pei, entitled "System and Method for Detecting Hidden Atrial Events for use with Automatic Mode Switching within an Implantable Medical Device," which might be adapted for use with the present invention.

At step 258, the pacer/ICD then compares any increase in IACD to a corresponding two-standard-deviation IACD threshold (or to a threshold set during a training period, as discussed above) and also compares any increase in P-wave duration to a corresponding two-standard-deviation P-wave duration threshold (or to a threshold set during a training period, as discussed above). That is, the device uses the standard deviation in IACD calculated at step 256 from patient baseline values to assess whether a recent deviation in IACD exceeds two standard deviations. Likewise, the device uses the standard deviation in P-wave duration calculated at step 256 to assess whether a recent deviation in P-wave duration exceeds two standard deviations. Alternatively, other thresholds may be exploited, as already noted, such as percentage-based thresholds or fixed numerical thresholds. As one particular example, if IACD increases from 90 ms to 105 ms, such is indicative of a significantly increased IACD.

If both the IACD and the P-wave duration thresholds are exceeded, at step 260, then a cardiac-based (i.e. cardiogenic) elevation in LAP is confirmed, at step 262. (Alternatively, the device may be programmed to confirm the elevated LAP based on only one of these parameters exceeding its respective threshold.) Otherwise, a cardiac-based elevation in LAP is disconfirmed. That is, the device concludes that the elevation in zLAP detected at step 254 is likely due to non-cardiogenic factors, such as pneumonia.

Assuming the elevated LAP is confirmed, then the pacer/ICD initiates any of a variety of actions at step 266, such as to: deliver diuretics or other medications; generate warnings; adjust or initiate LA pacing to improve hemodynamics; deliver CRT; evaluate HF severity; and/or record suitable diagnostics. Insofar as LA pacing is concerned, if the system is equipped with an LA electrode in the CS (either stand alone or as an element of the LV lead), LA pacing may be used to enhance hemodynamics, while pausing pacing periodically to measure IACD.

Insofar as CRT is concerned, this particular therapy seeks to normalize asynchronous cardiac electrical activation and the resultant asynchronous contractions by delivering synchronized pacing stimulus to the ventricles using pacemakers or ICDs equipped with biventricular pacing capability. The pacing stimulus is typically synchronized so as to help to improve overall cardiac function. This may have the additional beneficial effect of reducing the susceptibility to life-threatening tachyarrhythmias. CRT and related therapies are discussed in, for example, U.S. Pat. No. 6,643,546 to Mathis, et al., entitled "Multi-Electrode Apparatus And Method For Treatment Of Congestive Heart Failure"; U.S. Pat. No. 6,628,988 to Kramer, et al., entitled "Apparatus And Method For Reversal Of Myocardial Remodeling With Electrical Stimulation"; and U.S. Pat. No. 6,512,952 to Stahmann, et al., entitled "Method And Apparatus For Maintaining Synchronized Pacing."

Insofar as HF severity is concerned, the amount of increase in LAP, as well as the amount of increase in IACD and P-wave duration, can be exploited to assess the severity of any HF within the patient. This may be combined with other HF assessment techniques. See, for example, heart failure detection/evaluation techniques set forth in U.S. patent application Ser. No. 11/559,235, cited above. See, also, U.S. Pat. No. 6,748,261, entitled "Implantable medical device for and Method of Monitoring Progression or Regression of Heart Disease by Monitoring Interchamber Conduction Delays"; U.S. Pat. No. 6,741,885, entitled "Implantable Cardiac Device for Managing the Progression of Heart Disease and Method"; U.S. Pat. No. 6,643,548, entitled "Implantable medical device for Monitoring Heart Sounds to Detect Progression and Regression of Heart Disease and Method Thereof"; U.S. Pat. No. 6,572,557, entitled "System and Method for Monitoring Progression of Cardiac Disease State using Physiologic Sensors"; and U.S. Pat. No. 6,480,733, entitled "Method for Monitoring Heart Failure," each assigned to Pacesetter, Inc.

Figure 6:
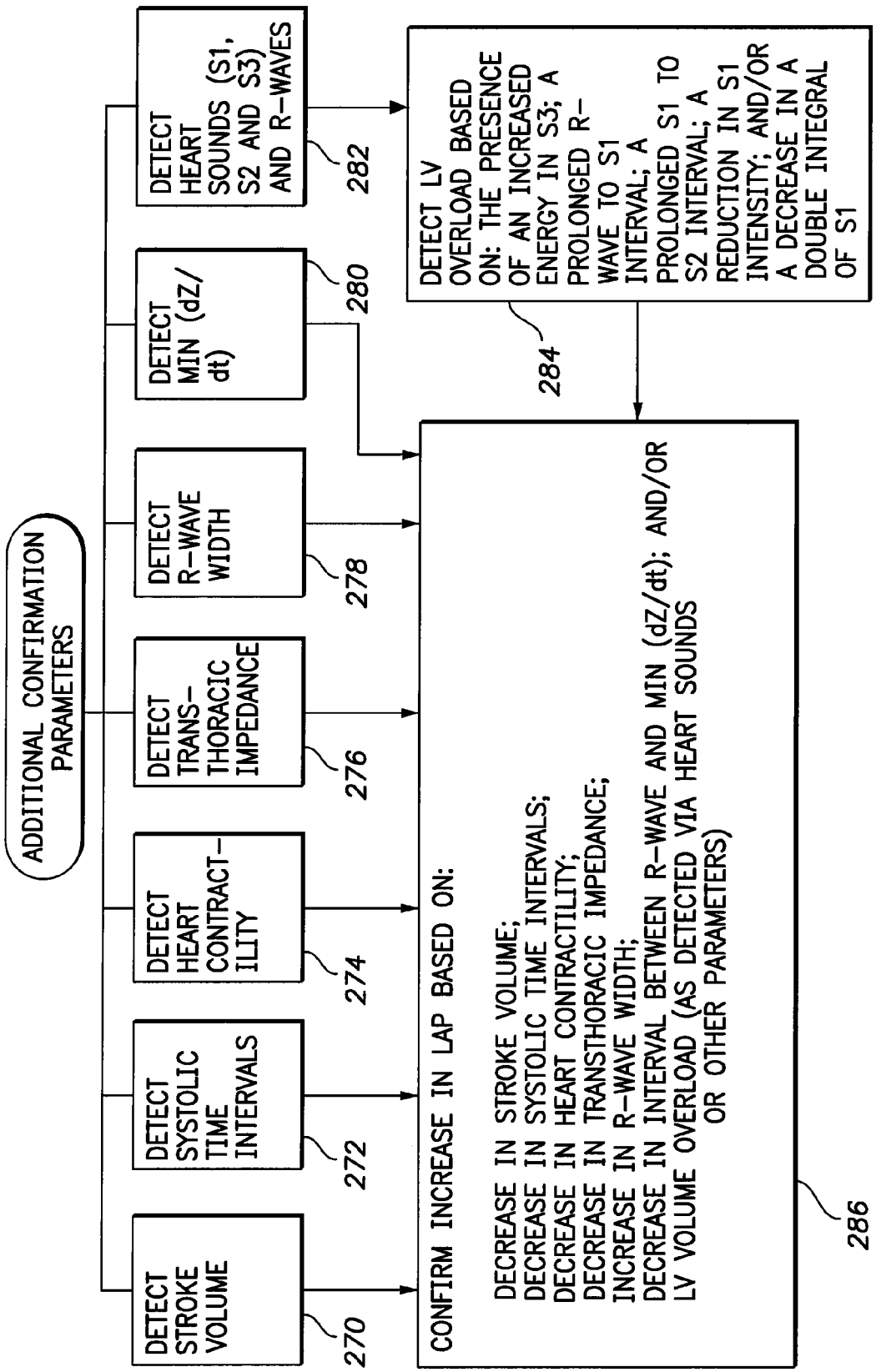
FIG. 6 is a flow diagram illustrating additional parameters that the device of FIG. 1 can use to confirm the detection of an elevated LAP.

FIG. 6 illustrates various other parameters that can be used, individually or in combination, to confirm an elevated LAP. At step 270, stroke volume is detected or estimated by the implantable device. A decrease in stroke volume is consistent with an increase in LAP. For techniques for assessing stroke volume, see, for example: U.S. patent application Ser. No. 11/378,604, filed Mar. 16, 2006, of Kroll et al., entitled, "System and Method for Detecting Arterial Blood Pressure based on Aortic Electrical Resistance using an Implantable Medical Device." See, also, U.S. patent application Ser. No. 11/267,665, filed Nov. 4, 2005, of Kil et al., entitled "System and Method for Measuring Cardiac Output via Thermal Dilution using an Implantable Medical Device with Thermistor Implanted in Right Ventricle."

At step 272, the implantable device detects systolic time intervals, i.e. any of a variety of intervals for assessing LV performance, particularly LV ejection time, electromechanical systole, and pre-ejection period, which may be detected using otherwise conventional techniques. In general, any change in these parameters indicative of a decrease in LV performance is consistent with an elevated LAP.

At step 274, heart contractility is assessed by the implantable device. A decrease in contractility is consistent with elevated LAP. Techniques for assessing contractility are described in: U.S. Pat. No. 5,800,467 to Park et al. entitled "Cardio-Synchronous Impedance Measurement System for an Implantable Stimulation Device."

At step 276, trans-thoracic impedance is measured by the implantable device. In this regard, an overall drop in impedance is associated with fluid retention and hence also associated with elevated LAP. Trans-thoracic impedance can be detected by a pacer/ICD from LV tip to case or by the electrodes of a suitably-equipped sub-Q device. Note also that impedance measured by a sub-Q device with electrodes on the implant case can also resolve contractility changes, and systolic time intervals as well as provide a stoke volume surrogate. Adding short sub-Q small diameter impedance wires can be used to enhance both subcutaneous ECG sensing and can further enhance the measurement and exceed the value, precision, and accuracy of classic impedance cardiography. These signals can provide time intervals that correlate to aortic valve opening, aortic valve closure, and maximal rate of ejection (dZ/dt min) as well as the time interval between R-wave and dZ/dt min. This interval is directly related to dP/dt max. All of these parameters are altered by LV fluid overload. In addition, the enhanced sensing dipole provided by sub-Q wires (assuming the device is so equipped) improves P-wave resolution as well as R-wave resolution thus enhancing the ability of the sub-Q device to measure P-wave and R-wave duration.

At step 278, the device detects R-wave duration. An increase in R-wave duration is also consistent with an increase in LAP. This feature is particular useful in sub-Q devices that may not be as effective at detecting P-waves.

At step 280, the device detects min dZ/dt, which as noted is related to max dP/dt. Moreover, the interval beaten the R-wave and the min dZ/dt time can be used to confirm an elevated LAP. In particular, this interval increases with increasing LAP.

At step 282, the implantable device detects heart sounds using an accelerometer or acoustic sensor. For example, an accelerometer can be used to detect the presence of an increased energy of a third heart sound (S3) indicating diastolic filling abnormalities. A prolonged R-wave to first heart sound (S1) interval indicates prolonged electromechanical delay and isovolumic period. A shortened S1 to second heart sound (S2) indicates shortened ventricular systole. A prolonged Q-wave to S1 suggests a prolonged electromechanical activation. A reduction in S1 intensity is related to reduced contractility, while the amplitude of the double integral of S1 corresponds to stroke volume as well as the intensity of the contraction. As such, a decrease in the double integral of S1 is associated with elevated LAP. All of these parameters can be detected alone or together to further enhance the diagnosis of volume overload using a sub-Q monitor or other implanted device. See, e.g., U.S. Pat. Nos. 7,115,096 of Seijko et al. and 5,991,661 of Park and Bornzin.

These various parameters are assessed, alone or in combination, at step 286 to confirm the elevated LAP and indicate that the elevated LAP is due to cardiac causes (such as CHF) rather than noncardiac causes (such as pneumonia).

Although primarily described with respect to examples having a pacer/ICD or sub-Q monitor, other implantable medical devices may be equipped to exploit the techniques described herein. For the sake of completeness, an exemplary pacer/ICD will now be described, which includes components for performing the functions and steps already described.

Exemplary Pacer/ICD

Figure 8:
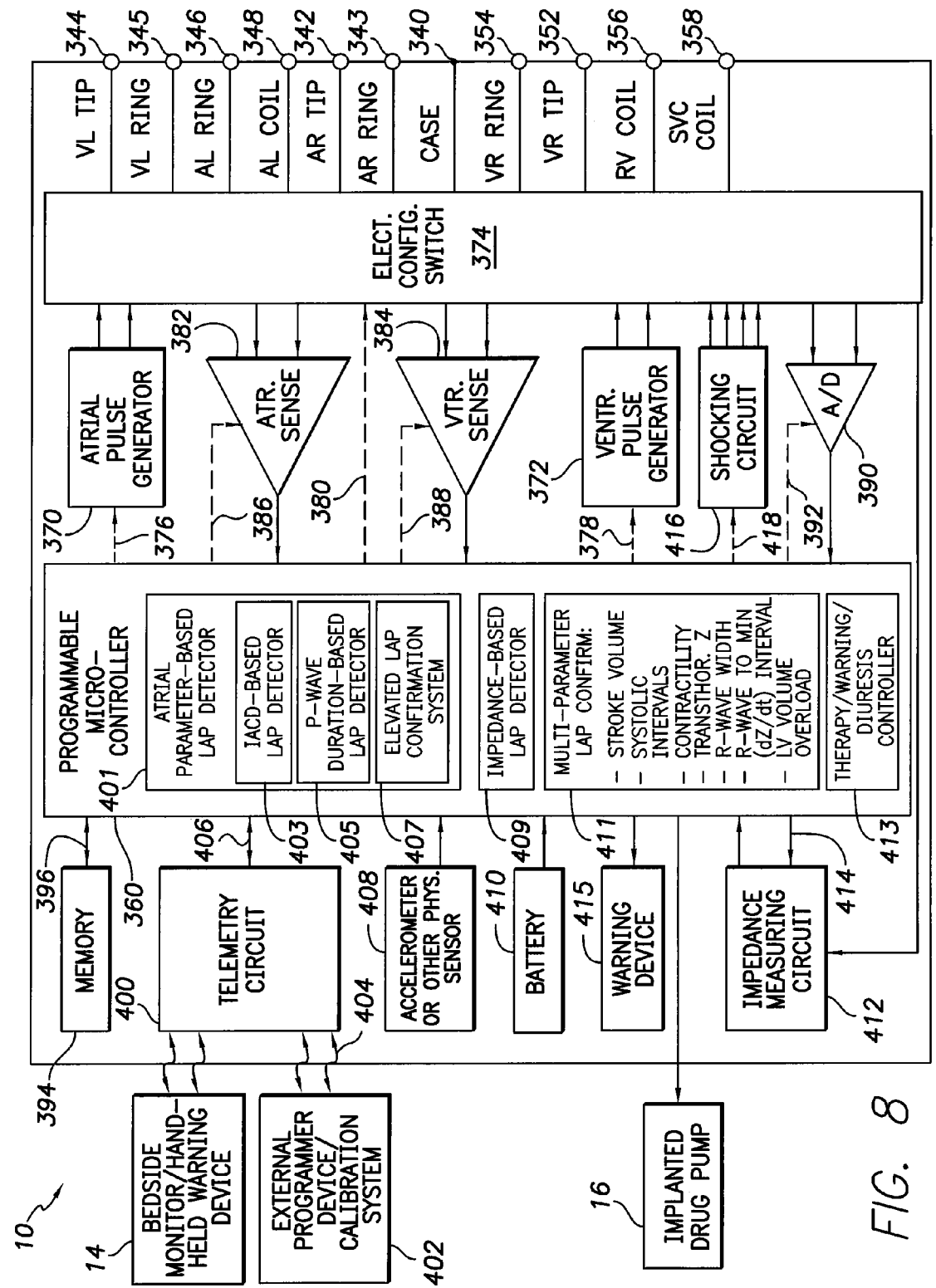
FIG. 8 a functional block diagram of the pacer/ICD of FIG. 7, illustrating basic circuit elements that provide cardioversion, defibrillation and/or pacing stimulation in the heart and particularly illustrating components for detecting, confirming and responding to an elevated LAP.

With reference to FIGS. 7 and 8, a description of an exemplary pacer/ICD will now be provided. FIG. 7 provides a simplified block diagram of the pacer/ICD, which is a dualchamber stimulation device capable of treating both fast and slow arrhythmias with stimulation therapy, including cardioversion, defibrillation, and pacing stimulation, and also capable of estimating LAP or other forms of cardiac pressure using impedance signals. To provide other atrial chamber pacing stimulation and sensing, pacer/ICD 10 is shown in electrical communication with a heart 312 by way of a left atrial lead 320 having an atrial tip electrode 322 and an atrial ring electrode 323 implanted in the atrial appendage. Pacer/ICD 10 is also in electrical communication with the heart by way of a right ventricular lead 330 having, in this embodiment, a ventricular tip electrode 332, a right ventricular ring electrode 334, a right ventricular (RV) coil electrode 336, and a superior vena cava (SVC) coil electrode 338. Typically, the right ventricular lead 330 is transvenously inserted into the heart so as to place the RV coil electrode 336 in the right ventricular apex, and the SVC coil electrode 338 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a CS lead 324 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary CS lead 324 is designed to receive atrial and ventricular cardiac signals and to deliver left ventricular pacing therapy using at least a left ventricular tip electrode 326 and a LV ring electrode 325, left atrial pacing therapy using at least a left atrial ring electrode 327, and shocking therapy using at least a left atrial coil electrode 328. With this configuration, biventricular pacing can be performed. Also, LA pacing may be delivered to improve hemodynamics via electrode 328. Although only three leads are shown in FIG. 7, it should also be understood that additional leads (with one or more pacing, sensing and/or shocking electrodes) might be used and/or additional electrodes might be provided on the leads already shown. An interventricular conduction delay 101, already discussed, is also shown in FIG. 7.

A simplified block diagram of internal components of pacer/ICD 10 is shown in FIG. 8. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 340 for pacer/ICD 10, shown schematically in FIG. 8, is often referred to as the "can", "case" or "case electrode" and may be programmably selected to act as the return electrode for all "unipolar" modes. The housing 340 may further be used as a return electrode alone or in combination with one or more of the coil electrodes, 328, 336 and 338, for shocking purposes. The housing 340 further includes a connector (not shown) having a plurality of terminals, 342, 343, 344, 345, 346, 348, 352, 354, 356 and 358 (shown schematically and, for convenience, the names of the electrodes to which they are connected are shown next to the terminals). As such, to achieve right atrial sensing and pacing, the connector includes at least a right atrial tip terminal ($A_R$ TIP) 342 adapted for connection to the atrial tip electrode 322 and a right atrial ring ($A_R$ RING) electrode 343 adapted for connection to right atrial ring electrode 323. To achieve left chamber sensing, pacing and shocking, the connector includes at least a left ventricular tip terminal ($V_L$ TIP) 344, a left ventricular ring terminal ($V_L$ RING) 345, a left atrial ring terminal ($A_L$ RING) 346, and a left atrial shocking terminal ($A_L$ COIL) 348, which are adapted for connection to the left ventricular ring electrode 326, the left atrial ring electrode 327, and the left atrial coil electrode 328, respectively. To support right chamber sensing, pacing and shocking, the connector further includes a right ventricular tip terminal ($V_R$ TIP) 352, a right ventricular ring terminal ($V_R$ RING) 354, a right ventricular shocking terminal ($V_R$ COIL) 356, and an SVC shocking terminal (SVC COIL) 358, which are adapted for connection to the right ventricular tip electrode 332, right ventricular ring electrode 334, the $V_R$ coil electrode 336, and the SVC coil electrode 338, respectively.

At the core of pacer/ICD 10 is a programmable microcontroller 360, which controls the various modes of stimulation therapy. As is well known in the art, the microcontroller 360 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 360 includes the ability to process or monitor input signals (data) as controlled by a program code stored in a designated block of memory. The details of the design and operation of the microcontroller 360 are not critical to the invention. Rather, any suitable microcontroller 360 may be used that carries out the functions described herein. The use of microprocessor-based control circuits for performing timing and data analysis functions are well known in the art.

As shown in FIG. 8, an atrial pulse generator 370 and a ventricular pulse generator 372 generate pacing stimulation pulses for delivery by the right atrial lead 320, the right ventricular lead 330, and/or the CS lead 324 via an electrode configuration switch 374. It is understood that in order to provide stimulation therapy in each of the four chambers of the heart, the atrial and ventricular pulse generators, 370 and 372, may include dedicated, independent pulse generators, multiplexed pulse generators or shared pulse generators. The pulse generators, 370 and 372, are controlled by the microcontroller 360 via appropriate control signals, 376 and 378, respectively, to trigger or inhibit the stimulation pulses.

The microcontroller 360 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 374 includes a plurality of switches for connecting the desired electrodes to the appropriate I/O circuits, thereby providing complete electrode programmability. Accordingly, the switch 374, in response to a control signal 380 from the microcontroller 360, determines the polarity of the stimulation pulses (e.g., unipolar, bipolar, combipolar, etc.) by selectively closing the appropriate combination of switches (not shown) as is known in the art.

Atrial sensing circuits 382 and ventricular sensing circuits 384 may also be selectively coupled to the right atrial lead 320, CS lead 324, and the right ventricular lead 330, through the switch 374 for detecting the presence of cardiac activity in each of the four chambers of the heart. Accordingly, the atrial (ATR. SENSE) and ventricular (VTR. SENSE) sensing circuits, 382 and 384, may include dedicated sense amplifiers, multiplexed amplifiers or shared amplifiers. The switch 374 determines the "sensing polarity" of the cardiac signal by selectively closing the appropriate switches, as is also known in the art. In this way, the clinician may program the sensing polarity independent of the stimulation polarity. Each sensing circuit, 382 and 384, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 382 and 384, are connected to the microcontroller 360 which, in turn, are able to trigger or inhibit the atrial and ventricular pulse generators, 370 and 372, respectively, in a demand fashion in response to the absence or presence of cardiac activity in the appropriate chambers of the heart.

For arrhythmia detection, pacer/ICD 10 utilizes the atrial and ventricular sensing circuits, 382 and 384, to sense cardiac signals to determine whether a rhythm is physiologic or pathologic. As used in this section, "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 360 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 390. The data acquisition system 390 is configured to acquire intracardiac electrogram signals, convert the raw analog data into a digital signal, and store the digital signals for later processing and/or telemetric transmission to an external device 402. The data acquisition system 390 is coupled to the right atrial lead 320, the CS lead 324, and the right ventricular lead 330 through the switch 374 to sample cardiac signals across any pair of desired electrodes. The microcontroller 360 is further coupled to a memory 394 by a suitable data/address bus 396, wherein the programmable operating parameters used by the microcontroller 360 are stored and modified, as required, in order to customize the operation of pacer/ICD 10 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 394 through a telemetry circuit 400 in telemetric communication with the external device 402, such as a programmer, transtelephonic transceiver or a diagnostic system analyzer. The telemetry circuit 400 is activated by the microcontroller by a control signal 406. The telemetry circuit 400 advantageously allows intracardiac electrograms and status information relating to the operation of pacer/ICD 10 (as contained in the microcontroller 360 or memory 394) to be sent to the external device 402 through an established communication link 404. Pacer/ICD 10 further includes an accelerometer or other physiologic sensor 408, commonly referred to as a "rate-responsive" sensor because it is typically used to adjust pacing stimulation rate according to the exercise state of the patient. However, the physiological sensor 408 may further be used to detect changes in cardiac output, changes in the physiological condition of the heart, or diurnal changes in activity (e.g., detecting sleep and wake states) and to detect arousal from sleep. Accordingly, the microcontroller 360 responds by adjusting the various pacing parameters (such as rate, AV delay, V-V delay, etc.) at which the atrial and ventricular pulse generators, 370 and 372, generate stimulation pulses. While shown as being included within pacer/ICD 10, it is to be understood that the physiologic sensor 408 may also be external to pacer/ICD 10, yet still be implanted within or carried by the patient. A common type of rate responsive sensor is an activity sensor incorporating an accelerometer or a piezoelectric crystal, which is mounted within the housing 340 of pacer/ICD 10. Other types of physiologic sensors are also known, for example, sensors that sense the oxygen content of blood, respiration rate and/or minute ventilation, pH of blood, ventricular gradient, stroke volume, contractility, heart sounds, etc.

The pacer/ICD additionally includes a battery 410, which provides operating power to all of the circuits shown in FIG. 8. The battery 410 may vary depending on the capabilities of pacer/ICD 10. If the system only provides low voltage therapy, a lithium iodine or lithium copper fluoride cell typically may be utilized. For pacer/ICD 10, which employs shocking therapy, the battery 410 should be capable of operating at low current drains for long periods, and then be capable of providing high-current pulses (for capacitor charging) when the patient requires a shock pulse. The battery 410 should also have a predictable discharge characteristic so that elective replacement time can be detected. Accordingly, appropriate batteries are employed.

As further shown in FIG. 8, pacer/ICD 10 is shown as having an impedance measuring circuit 412, which is enabled by the microcontroller 360 via a control signal 414. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 412 is advantageously coupled to the switch 474 so that any desired electrode may be used. The impedance measuring circuit 412 also detects the impedance signals discussed above if zLAP is to be estimated. That is, impedance measuring circuit 412 is an electrical impedance (Z) detector operative to detect an electrical impedance (Z) signal within the patient along at least one sensing vector wherein impedance is affected by cardiac pressure.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 360 further controls a shocking circuit 416 by way of a control signal 418. The shocking circuit 416 generates shocking pulses of low (up to 0.5 joules), moderate (0.5-10 joules) or high energy (11 to 40 joules), as controlled by the microcontroller 360. Such shocking pulses are applied to the heart of the patient through at least two shocking electrodes, and as shown in this embodiment, selected from the left atrial coil electrode 328, the RV coil electrode 336, and/or the SVC coil electrode 338. The housing 340 may act as an active electrode in combination with the RV electrode 336, or as part of a split electrical vector using the SVC coil electrode 338 or the left atrial coil electrode 328 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 11-40 joules), delivered asynchronously (since R-waves may be too disorganized), and pertaining exclusively to the treatment of fibrillation. Accordingly, the microcontroller 360 is capable of controlling the synchronous or asynchronous delivery of the shocking pulses.

Insofar as LAP estimation is concerned, the microcontroller includes an atrial parameter-based LAP detector 401 operative to detect LAP based on atrial electrocardiac parameters derived using the techniques described above. In this example, detector 401 includes: an IACD-based LAP detector 403 operative to assess changes in LAP based on IACDs measured within the patient and a P-wave duration-based LAP detector 405 operative to assess changes in LAP based on P-wave duration.

Additionally, an impedance-based LAP detector 409 is provided to assess LAP via zLAP techniques, as discussed above. If an elevated LAP is detected via impedance, then an elevated LAP confirmation system 407 may be exploited to confirm the elevated LAP using the techniques of FIGS. 4-5. As discussed with reference to FIG. 6, a variety of other parameters may be used to confirm an elevated LAP. This is indicated by multiple-parameter LAP confirmation unit 411.

Warning signals are generated, when appropriate, by a therapy/warning/diuresis controller 413 then relayed to the bedside monitor 16 via telemetry system 400 or to external programmer 402 (or other external calibration system.) An internal warning device 415 may also be used to generate warning signals. Controller 413 also controls an implantable drug pump, if one is provided, to deliver appropriate medications such as diuretics. Controller 413 also controls LA pacing or CRT, as discussed above. Terminals for connecting the implanted drug pump to the pacer/ICD are not separately shown. Diagnostic data pertaining to LAP, CHF, therapy adjustments, etc., is stored in memory 394.

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

Exemplary Sub-Q ILR

For the sake of completeness, a sub-Q ILR monitor 510 is shown in FIG. 9, which may be equipped to perform many of the LAP assessment functions described above based on signals sensed by its electrodes (not separately shown.) As already explained, the capability of the device to implement the functions discussed above depends in part on the sensing capabilities of the device. The device of FIG. 9 is equipped to detect impedance signals from which a form of zLAP can be assessed and to detect sufficiently accurate atrial electrocardiac signals from which IACD and P-wave duration can be assessed. In particular, device 510 includes a set of small diameter impedance wires 512 for enhancing subcutaneous ECG sensing. Impedance signals derived from these wires are used by the device to provide many of the confirmation time intervals discussed above, such as those that correlate to aortic valve opening, aortic valve closure, maximal rate of ejection (dZ/dt min) as well as the time interval between R-wave and dZ/dt min. All of these parameters are altered by LV fluid overload. In addition, the enhanced sensing dipole provided by sub-Q wires improves P-wave resolution as well as R-wave resolution thus enhancing the ability of the sub-Q device to measure P-wave and R-wave duration. That is, wires 512 are also used to sense subcutaneous ECG signals from which P-wave duration and IACD are derived, as well as other ECG parameters.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for use with an implantable medical device for implant within a patient, the method comprising:
   sensing electrocardiac signals within the patient;
   detecting atrial parameters within the electrocardiac signals that are affected by left atrial pressure (LAP);
   detecting changes in LAP within the patient based on the atrial parameters;
   detecting physiological signals representative of left ventricular (LV) overload within the patient; and
   wherein the detection of changes in LAP is confirmed based on the detected LV overload.

2. The method of claim 1 wherein detecting atrial parameters affected by LAP includes detecting one or more of: an intra-atrial conduction delay (IACD) and an atrial depolarization event (P-wave) duration.

3. The method of claim 2 wherein detecting changes in LAP within the patient based on the atrial parameters includes associating an increase in IACD with an increase in LAP.

4. The method of claim 2 wherein detecting changes in LAP within the patient based on the atrial parameters includes associating an increase in P-wave duration with an increase in LAP.

5. The method of claim 2 further including calibrating changes in one or both of IACD and P-wave duration to changes in LAP.

6. The method of claim 2 further including:
   detecting impedance (Z) signals within the patient;
   estimating left atrial pressure (LAP) based on impedance (zLAP); and
   detecting changes in LAP within the patient based on zLAP.

7. The method of claim 6 further including using the atrial parameters to confirm a detection of changes in LAP initially made based on zLAP.

8. A method for use with an implantable medical device for implant within a patient, the method comprising:
   sensing electrocardiac signals within the patient;
   detecting atrial parameters within the electrocardiac signals that are affected by left atrial pressure (LAP);
   detecting changes in LAP within the patient based on the atrial parameters;
   detecting changes in one or more of heart contractility, systolic time intervals and stroke volumes; and confirming the detection of changes in LAP based on one or more of heart contractility, systolic time intervals and stroke volumes.

9. A method for use with an implantable medical device for implant within a patient, the method comprising:
- sensing electrocardiac signals within the patient;
- detecting atrial parameters within the electrocardiac signals that are affected by left atrial pressure (LAP);
- detecting changes in LAP within the patient based on the atrial parameters;
- detecting ventricular depolarization events (R-waves) within the electrocardiac signals;
- detecting impedance (Z);
- detecting a time rate of change in impedance (dZ/dt);
- measuring an interval between the R-wave and a minimum value of dZ/dt; and
- confirming the detection of changes in LAP based on changes in the interval.

10. The method of claim 9 wherein impedance is detected between a supraventricular (SVC) coil and a device housing electrode.

11. A method for use with an implantable medical device for implant within a patient, the method comprising:
- sensing electrocardiac signals within the patient;
- detecting atrial parameters within the electrocardiac signals that are affected by left atrial pressure (LAP);
- detecting changes in LAP within the patient based on the atrial parameters;
- detecting ventricular depolarization events (R-waves) within the electrocardiac signals;
- detecting changes in R-wave duration; and
- confirming the detection of changes in LAP based on changes in R-wave duration.

* * * * *